US005767387A

United States Patent [19]
Wang

[11] Patent Number: 5,767,387
[45] Date of Patent: Jun. 16, 1998

[54] CHROMATOGRAPH HAVING PNEUMATIC DETECTOR

[75] Inventor: Tak Kui Wang, Havertown, Pa.

[73] Assignee: Hewlett-Packard Co., Palo Alto, Calif.

[21] Appl. No.: 731,942

[22] Filed: Oct. 22, 1996

[51] Int. Cl.[6] .................................................. G01N 30/04
[52] U.S. Cl. ............................................................ 73/23.42
[58] Field of Search ............................. 73/23.21, 23.22, 73/23.24, 23.25, 23.27, 23.36, 23.42; 95/82

[56] References Cited

U.S. PATENT DOCUMENTS

| | | |
|---|---|---|
| 3,354,696 | 11/1967 | Novak et al. |
| 4,006,624 | 2/1977 | Annino et al. ............... 73/23.1 |
| 4,033,171 | 7/1977 | Karas et al. |
| 4,095,455 | 6/1978 | Karas et al. ................. 73/23.1 |
| 4,379,402 | 4/1983 | Harman ....................... 73/23 |
| 4,479,380 | 10/1984 | Novotny et al. ............. 73/61.1 C |
| 4,814,089 | 3/1989 | Kumar ......................... 210/659 |
| 4,822,250 | 4/1989 | Kumar ......................... 210/198.2 |
| 4,871,453 | 10/1989 | Tsbouchii et al. ........... 417/45 |
| 4,994,096 | 2/1991 | Klein et al. .................. 55/20 |
| 5,108,466 | 4/1992 | Klein et al. .................. 55/20 |
| 5,476,000 | 12/1995 | Wang et al. .................. 364/510 |
| 5,524,084 | 6/1996 | Hinshaw et al. ............. 73/23.36 X |
| 5,545,252 | 8/1996 | Henderson et al. .......... 73/23.7 |
| 5,583,281 | 12/1996 | Yu ............................... 73/23.42 |

*Primary Examiner*—Robert Raevis
*Assistant Examiner*—Jay L. Politzer
*Attorney, Agent, or Firm*—Mark Z. Dudley

[57] ABSTRACT

A chromatograph includes an injector for receiving a sample and a pressurized carrier fluid flow and in response providing a sample/fluid mixture; a separation column located in a temperature-controlled zone for receiving the sample/fluid mixture and for providing a column effluent stream; a pneumatic detector having an orifice for receiving the effluent stream; means for sensing the volumetric flow rate of the fluid mixture entering the column and for generating a respective flow rate signal; means for sensing the column input pressure and generating a respective input pressure signal; an electronic pneumatic controller including means for receiving the flow rate signal and input pressure signal and for controlling in response the input pressure and the volumetric flow rate of the carrier fluid; and means for detecting a change in the pressure of the effluent stream at the orifice in response to a change in the density of the effluent stream passing through the orifice and for generating a representative output signal, whereby one or more characteristics of the effluent stream that are related to the density of the effluent stream are represented by the output signal. The temperature of the temperature-controlled zone, and some or all of the input and output pressures and the carrier fluid volumetric flow rate are controlled by the electronic pressure controller, which reduces unwanted flow rate variation in the fluid stream that is subject to detection is greatly reduced. The sensitivity of the pneumatic detector to such unwanted flow rate variations is thus mitigated by the operation of the electronic pneumatic controller.

12 Claims, 10 Drawing Sheets

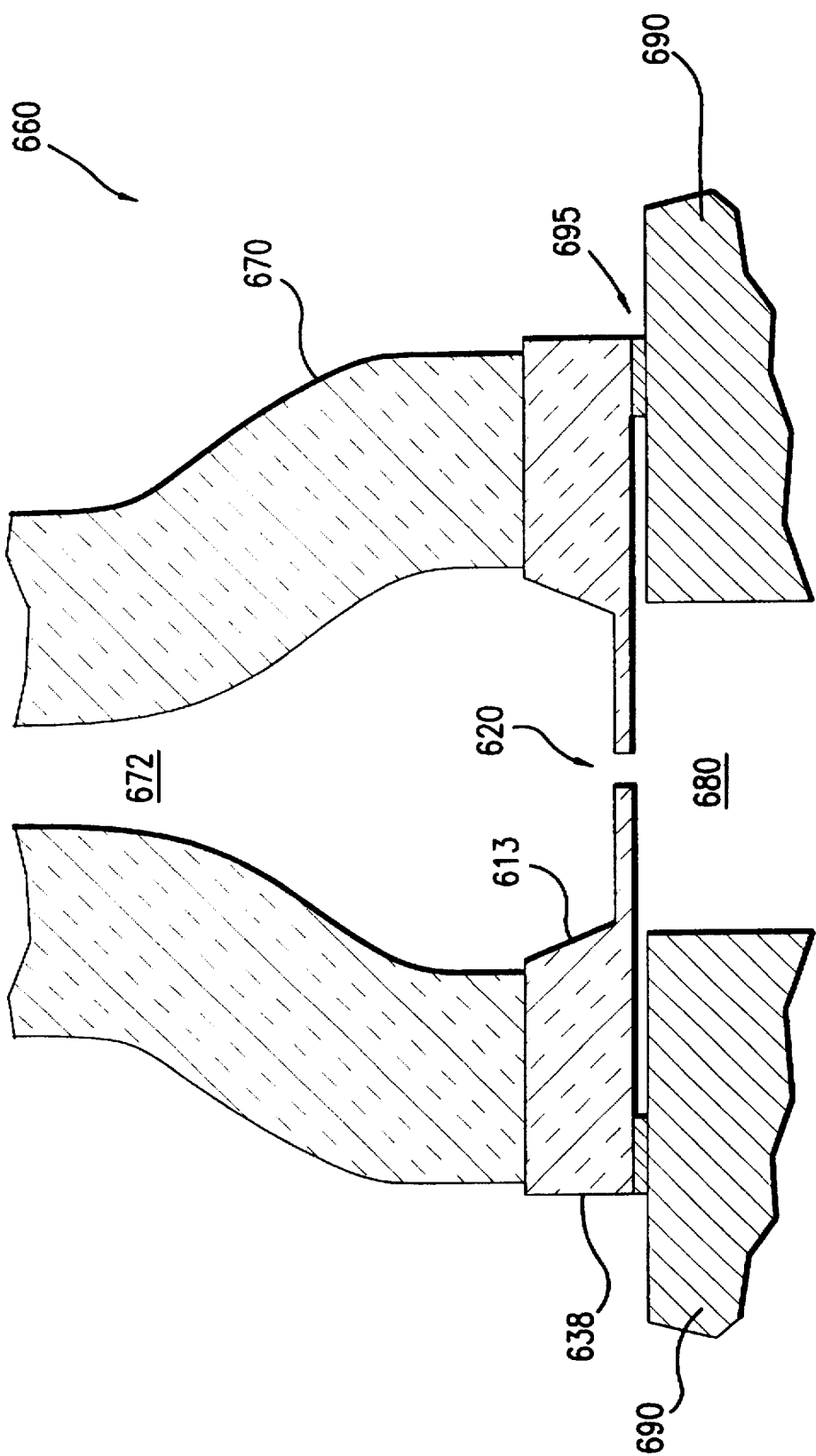

CHROMATOGRAPH HAVING PNEUMATIC DETECTOR

FIELD OF THE INVENTION

The present invention relates to methods and apparatus for use in analytical instrumentation for the detection of an analyte in a carrier fluid, and for identification of the composition of the carrier fluid itself.

BACKGROUND OF THE INVENTION

Analytical instruments such as a gas chromatograph are known for use in determining the chemical composition of a sample, which may be gaseous or a vaporized liquid, and which is typically injected into a carrier fluid stream. In one type of gas chromatograph, a fluid mixture of a sample and a carrier fluid is directed through a separation column. The typical separation column is a long capillary tube having a stationary phase coating on the interior of the column. The interaction of the constituent compounds in the sample with the stationary phase cause differing chemical compounds in the sample to travel through the separation column at different rates and to leave the separation column at different times. As compounds leave the separation column, their presence is sensed by a detector. The detector indicates the presence of compounds in the carrier gas by measuring one or more changes in the properties of the effluent gas. When a change in the gas property occurs, the timing of the change can indicate the type of the compound passing the detector, and the magnitude of the change can indicate the quantity of the compound. A compound of interest is typically called an analyte.

When a compound is mixed with the carrier gas, the density of the mixture is usually different from that of the pure carrier gas. One type of detector that has been proposed for use with gas chromatograph has been suggested to detect changes in the density of the effluent gas and accordingly has been described as a pneumatic detector. The pneumatic detector provides a measure of the change in the density of the mixture and thereby provides a measure of the presence and amount of the analyte in the effluent gas.

U.S. Pat. No. 3,354,696 teaches the use of means responsive to pressure drops developed by a bridge network of pneumatic resistors connected to the output of a column so as to detect changes in gas density.

U.S. Pat. No. 4,033,171 discloses a gas chromatograph having a pneumatic detector adapted to produce a component concentration measurement signal that is said to be relatively unaffected by changes in carrier flow rate. The detector comprises an orifice connected in the column output to produce a differential pressure signal responsive to fluid density and thus is said to be responsive to the concentration of a component in the fluid. The detector includes a capillary tube which is said to provide a flow-responsive pressure signal that is said to be used to compensate for the sensitivity of the detector to changes in flow velocity. However, the pneumatic arrangement taught in this approach have sufficiently high unswept volumes such that the analyte of interest may be diffused and lost. Also, the compensating action of the capillary tube may be sufficiently responsive in chromatographs that employ packed column or wide bore, high flow columns, but is likely to be unresponsive when used with chromatographs that employ narrow bore capillary columns.

Another significant shortcoming is due to manner in which the flow rate of the effluent fluid stream exiting a temperature-programmed column will vary over time; such a fluid stream is not well-suited for introduction into the flow-sensitive or pressure-sensitive pneumatic detectors previously known in the art. Variations in the flow rates or pressures of carrier fluids introduced into systems that use such detectors have resulted in variability and non-optimization of detector response.

Hence, the foregoing approaches have not found wide use in modern chromatography due in part to increasingly stringent demands for detectors that exhibit sufficient linearity, dynamic range, sensitivity, accuracy, versatility, and reliability. There thus exists a need for analytical instrumentation that employs an improved pneumatic detector wherein, among other factors, the flow rate of the carrier fluid entering the pneumatic detector is better controlled such that the detector response is made satisfactory for certain applications.

SUMMARY OF THE INVENTION

The advantages of the invention are achieved in a preferred embodiment of an analytical instrument, preferably provided in the form of a chromatograph, that includes an injector for receiving a sample and a pressurized carrier fluid flow and in response providing a sample/fluid mixture; a separation column located in a temperature-controlled zone for receiving the sample/fluid mixture and for providing a column effluent stream; a pneumatic detector having an orifice for receiving the effluent stream; means for sensing the volumetric flow rate of the fluid mixture entering the column and for generating a respective flow rate signal; means for sensing the column input pressure and generating a respective input pressure signal; an electronic pneumatic controller including means for receiving the flow rate signal and input pressure signal and for controlling in response the input pressure and the volumetric flow rate of the carrier fluid; and means for detecting a change in the pressure of the effluent stream at the orifice in response to a change in the density of the effluent stream passing through the orifice and for generating a representative output signal, whereby one or more characteristics of the effluent stream that are related to the density of the effluent stream are represented by the output signal.

In a first aspect of the invention, the temperature of the temperature-controlled zone, and some or all of the input and output pressures and the carrier fluid volumetric flow rate are controlled by the electronic pressure controller, which offers greater accuracy, sensitivity, and reliability than the controllers operable in pneumatic detection systems of the prior art. Accordingly, unwanted flow rate variation in the fluid stream subject to detection is greatly reduced. The sensitivity of the pneumatic detector to such unwanted flow rate variations is mitigated by the operation of the electronic pneumatic controller.

In another aspect of the invention, some or all of the fluid handling functions related to the fluid stream subject to detection are sensed and/or controlled via fluid-handling functional devices mounted on a planar manifold assembly. The planar manifold assembly includes one or more fluid-handling functional devices attached to a planar manifold. The planar manifold includes internal etched channels capable of bearing fluid flow, and thus provided in particular for bearing the carrier fluid flow. The fluid-handling functional device may be miniaturized and surface mounted to the planar manifold and may be constructed as a valve, operable in response to a control signal from the electronic pneumatic controller for controlling fluid flow or fluid pressure, or a fluid regulator, a fluid flow input or output line, or the like.

3

In another aspect of the invention, the orifice is provided in the form of a sharp-edge orifice integrated in a surface port on the planar manifold, wherein the surface port is in fluid communication with the column effluent fluid stream, such that the orifice is integrated with a surface of the planar manifold.

In another aspect of the invention, the orifice is provided in the form of a sharp-edge orifice integrated in a component portion of a fluid-handling functional device mounted on the planar manifold, whereby the component portion is in fluid communication with the column effluent fluid stream via an etched channel in the planar manifold, such that the orifice is integral with the component portion of the fluid-handling functional device.

In another aspect of the invention, the orifice is provided in the form of a sharp-edge orifice fabricated in a component portion of a micromachined orifice chip.

In another aspect of the invention, the orifice is provided in the form of a sharp-edge orifice fabricated in a component portion of a micromachined orifice chip that is closely adjacent to, and in fluid communication with, an etched channel in the planar manifold.

In another aspect of the invention, the orifice is provided in the form of a sharp-edge orifice integrated in a component portion of a pressure sensor, wherein the component portion is in fluid communication with the column effluent fluid stream and is responsive to the pressure of the column effluent fluid stream, whereby the pressure of the effluent stream at the orifice may be sensed.

In another aspect of the invention, the separation column is integrated within the planar manifold as a serpentine etched channel that is in fluid communication with the orifice.

BRIEF DESCRIPTION OF THE DRAWINGS

FIG. 6C is a side sectional view of a conduit attached to the separation column and joined to a micromachined orifice chip contemplated for use on a planar manifold in the planar manifold assembly of FIGS. 2-4.

DETAILED DESCRIPTION OF THE PREFERRED EMBODIMENT

The present invention will find useful application in a variety of analytical systems that are designed for detection of an analyte present in one or more fluid streams. Gases are the preferred fluids according to the practice of the present invention, and therefore the following description of the invention will include a description of the arrangement, construction, and operation of a novel pneumatic detector, and hence is particularly directed to the detection of an analyte in a fluid stream in a gas chromatographic analytical system (hereinafter, a chromatography. The teachings of the present invention may be applied to methods and apparatus for the detection of an analyte in a carrier fluid, and for identification of the composition of the carrier fluid itself.

For the purposes of the following description, the terms "fluid" and "pneumatic" will be considered to pertain to all types of gaseous fluids; "fluid-handling function" refers to at least one of the following functions with respect to one or more fluid streams: initiation, distribution, redirection, termination, pressure or flow rate control, and pressure or flow rate sensing; "fluid-handling functional device" refers to a device that provides one or more fluid-handling functions with respect to one or more fluid streams; "electronic pneumatic control" and "EPC" refers to programmed electronic control of fluids and fluid handling functions, among which are included the control of temperature, volumetric flow rate, and pressure of a fluid stream in a chromatograph, as for example in accordance with the invention disclosed by U.S. Pat. No. 4,994,096, and U.S. Pat. No. 5,108,466 in the names of Klein, et al., the disclosures of which are incorporated herein by reference, and to subsequent advances known in the art for programmed electronic pneumatic control of pressure, temperature, and/or flow rate of fluids in a chromatograph. U.S. Pat. No. 4,994,096, for example, disclosed an open loop system for controlling the flow rate of a carrier fluid in a system wherein a portion of the chromatographic column is subjected to a temperature profile.

In a significant departure from the prior art, the present invention will be understood to overcome many of the problems of chromatographic systems that employ pneumatic detectors, and also will be understood to provide improved detection of the molecular weight of a wide range of analytes present in a fluid stream.

In the embodiments illustrated in the Figures and described below, like nomenclature and numerical identifiers refer to identical or equivalent structures; a single line indicates an electronic signal line capable of transmitting an electronic signal; and double parallel lines indicate a pneumatic flow path capable of bearing a fluid stream.

Figure 1:
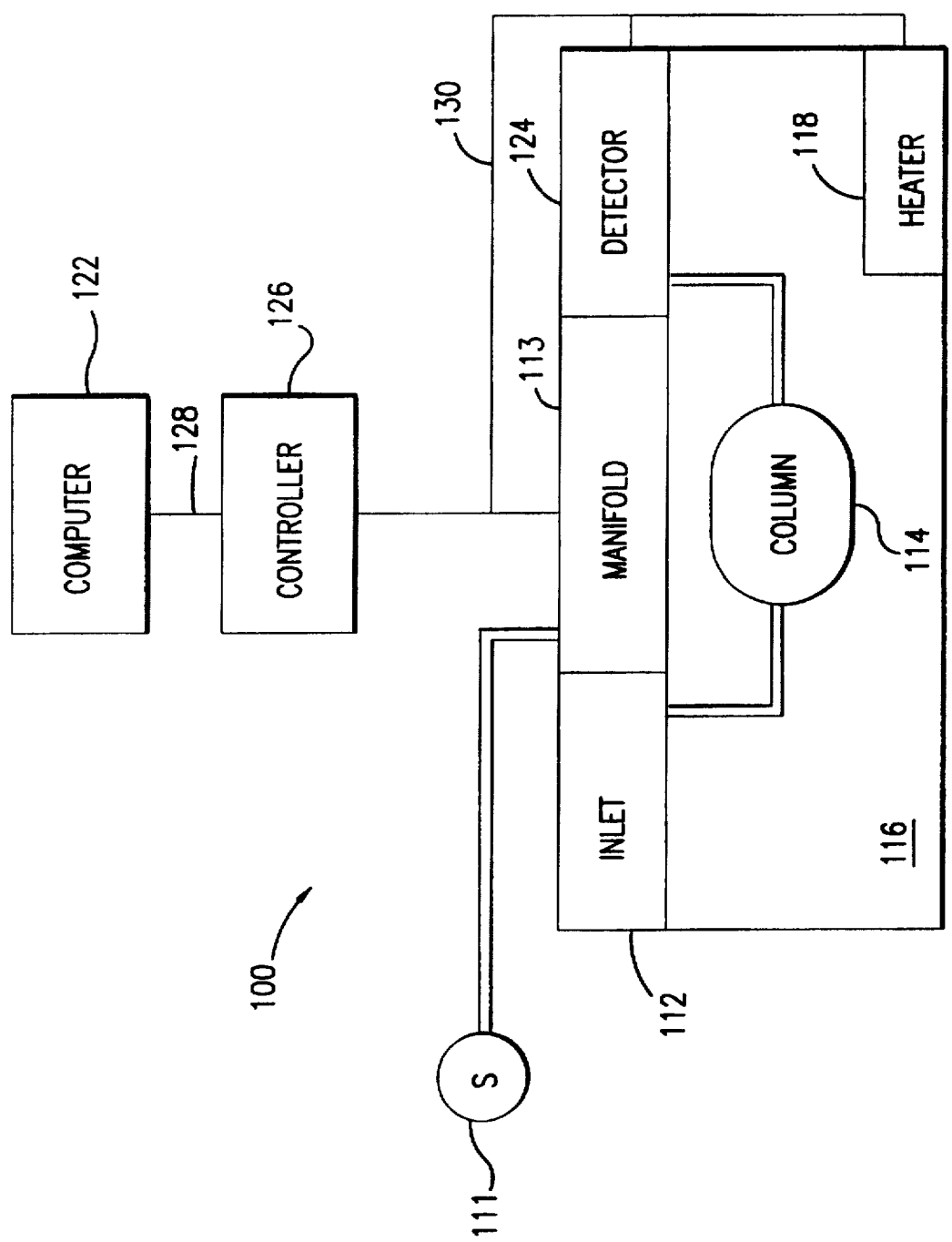
FIG. 1 is a simplified block diagram of an analytical instrument constructed as a chromatograph in accordance with the present invention.

A new and novel analytical instrument is shown in FIG. 1 and is generally designated chromatograph 100. In order to perform a chromatographic separation of a given sample compound, a sample is injected with a pressurized carrier fluid by means of an inlet 112. The carrier fluid supplied to inlet 112 is provided from a source 111 through one or more planar manifold assemblies 113, each of which serves in part to control and redirect a plurality of flows, including the carrier. The carrier and other fluids are directed to one or more fluid-handling functional devices such as valves, couplers, and the like in the planar manifold assembly 113 as will be described below. Certain fluid-handling functional devices, such as fittings, couplers, sensors, and the like in the planar manifold assembly 113 may be passive (such as a termination fitting) or active and hence operated under the control of a computer 122 and a pneumatic controller 126 by way of electronic pneumatic control signals provided on data and control lines 128, 130. Hence, in a particular feature of the present invention, the pneumatic controller 126 effects electronic pneumatic control of, among other things, temperature, fluid flow rate, fluid pressure, fluid flow regulation, and the continuity or discontinuity of flow of one or more fluid flow streams in chromatograph 100 in part by the use of fluid-handling functional devices as will be described below. As further example, the time during which a particular valve in the planar manifold assembly 113 will remain open and closed in relation to control signals received on the data and control line 130 and in accordance with certain operating conditions of the chromatograph 100. The data and control line 130 also allows the return of sense information from appropriate signal-interface electronics that may be integrated in, or connect to, certain ones of the fluid-handling functional devices such as the valves, sensors, etc. that are provided in the planar manifold assembly 113. Accordingly, the computer 122, pneumatic controller 126, and planar manifold 113 may be operated to effect a variety of fluid-handling functions with respect to a wide range of fluid flow rates and pressures at a level of accuracy, reliability, and consistency that heretofore has been difficult to achieve in prior art attempts to achieve identification of a carrier fluid or an analyte by use of a pneumatic detector.

A separation column 114 is positioned within an oven cavity 116. The sample/fluid mixture passing through column 114 is exposed to a temperature profile resulting in part from the operation of a heater 118 within oven cavity 116. During its passage through the column 114, the sample will separate into its components primarily due to differences in the interaction of each component with the column 114 at a given temperature. As the separated components exit the column 114, they are detected by a pneumatic detector 124. The detector 124 provides a detector output signal to controller 126 and computer 122 via respective data and control lines 128, 130.

By monitoring the operation of the chromatograph 100 by signals from certain components, such as the detector 124, the computer 122 can initiate and maintain the fluid handling functions required for an analysis. Computer 122 maintains overall control of all systems associated with chromatograph 100. It will be recognized that any particular embodiment of chromatograph 100 may include more systems than those described in relation to the present invention. It will also be understood that although computer 122 and pneumatic controller 126 are shown as individual blocks, such computer 122 and pneumatic controller 126 may be integrated and may individually or jointly include a central processing unit and associated software, firmware, and peripheral devices, such as random access memories, read-only memories, input/output isolation devices, clocks, and other related electronic components. In the preferred embodiment, the central processor used in computer 122 is a microprocessor. As such, computer 122 and/or controller 126 includes a memory in which electronic pneumatic control information and programming can be stored and retrieved by known methods. It will be appreciated that the pneumatic controller 126 can be implemented in other computing means, such as an embedded microprocessor or dedicated controller circuitry incorporated in the planar manifold assembly 113. Also, the programming (software, firmware, and the like) associated with computer 122 and pneumatic controller 126 as taught by the present invention will be readily understood from the description herein.

Figure 2:
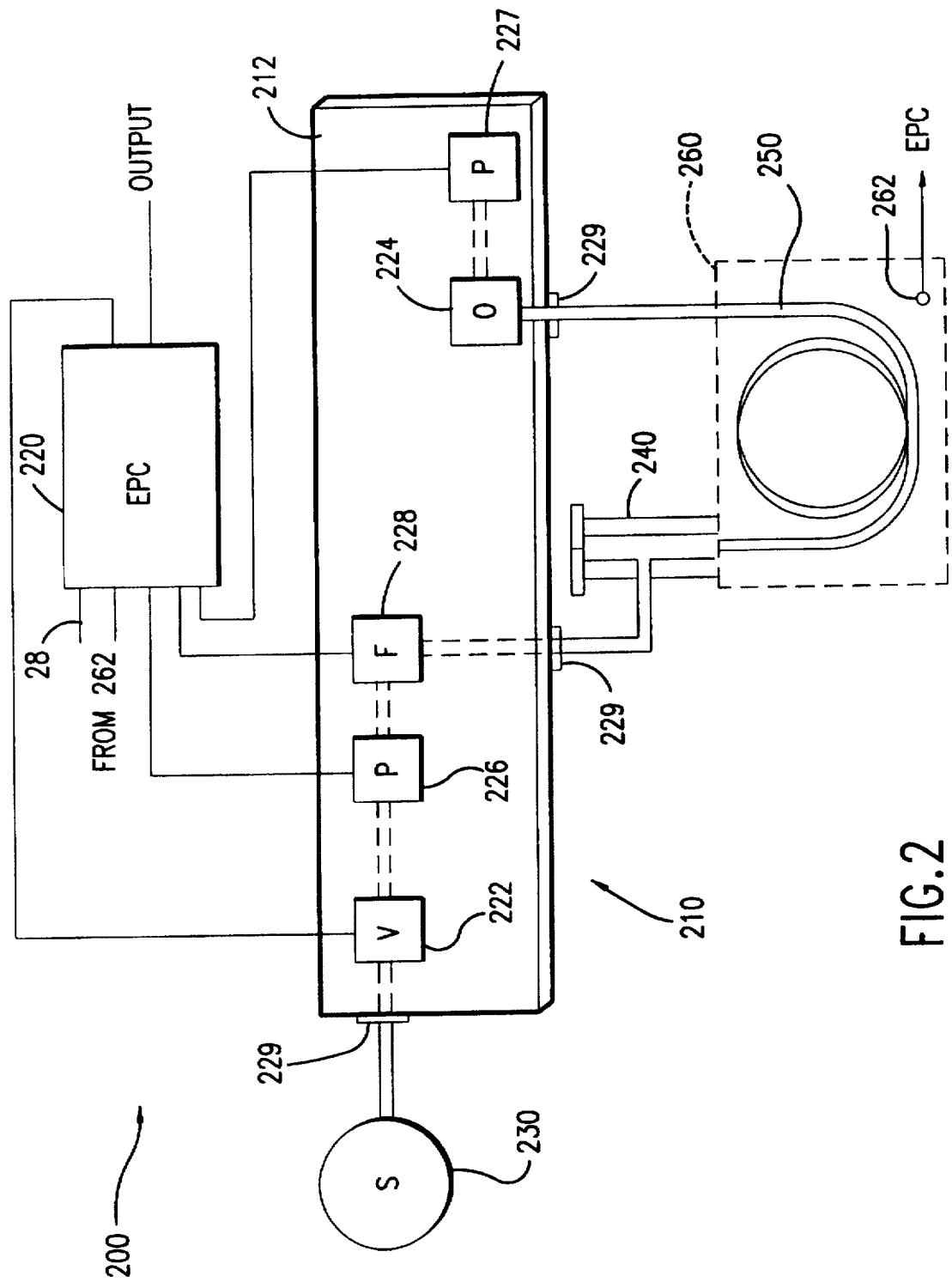
FIG. 2 is a simplified schematic view of an electronic pneumatic controller, planar manifold assembly, and related apparatus in a portion of the preferred embodiment of the analytical instrument of FIG. 1.
Figure 3:
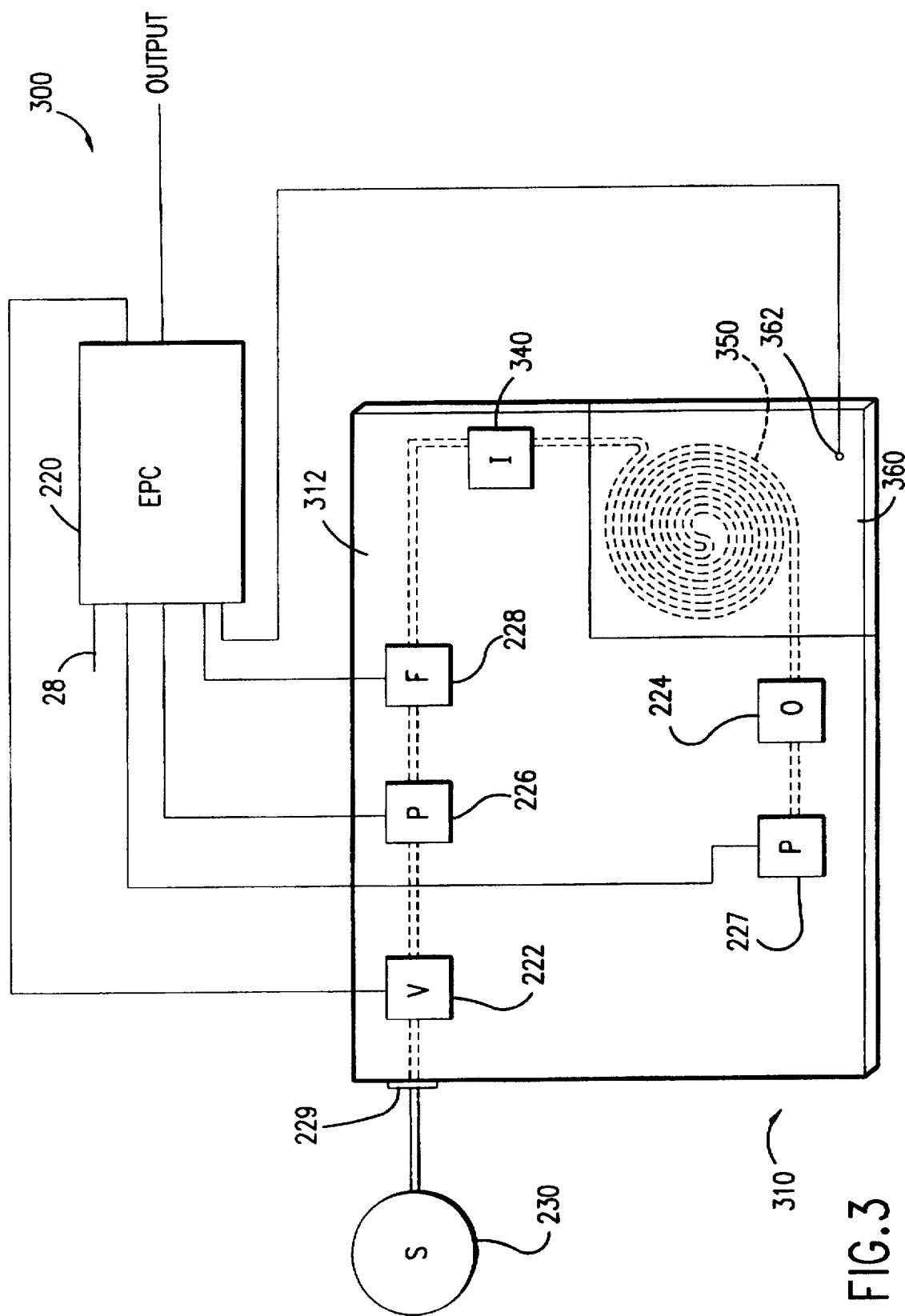
FIG. 3 is a simplified schematic view of an electronic pneumatic controller, alternative planar manifold assembly, and related apparatus in a portion of an alternative preferred embodiment of the analytical instrument of FIG. 1.

FIGS. 2 and 3 illustrate respective first and second preferred embodiments 200, 300 of the chromatograph 100 of FIG. 1. In the preferred embodiment, the chromatograph 100 is a Hewlett-Packard HP6890 gas chromatograph modified according to the teachings herein. The chromatograph 200 includes a planar manifold assembly 210 and controller 220 for effecting electronic pneumatic control specifically designed for fluid-handling functions in one or more planar manifolds 212 having mounted thereon various surface-mounted fluid-handling functional devices such as valve 222, pneumatic detector 224, pressure sensors 226, 227, flow controller 228, and couplers 229. The planar manifold assembly 210 is pneumatically coupled to at least one carrier fluid supply 230, one inlet 240 and one separation column 250. One or both of the inlet 240 and separation column 250 are installed in an oven cavity 260 that is temperature controlled by a suitable heater (not shown) according to a temperature sense signal provided to the controller 220 by a temperature sensor 262. In the chromatograph 300, a planar manifold assembly 310 includes planar manifold 312 having mounted thereon the aforementioned surface-mounted fluid-handling functional devices, the array of which now includes a surface-mounted inlet 340. Further, a separation column 350 formed as a serpentine, etched-channel conduit is provided within the planar manifold 312. One or both of the inlet 340 and separation column 350 are installed in temperature-controlled portion 360 of the planar manifold 312 which is temperature controlled by a suitable heater (not shown) according to a temperature sense signal provided to the controller 220 by an embedded or surface-mounted temperature sensor 362. In the illustrated embodiments 200, 300, the dashed parallel lines indicate a pneumatic flow path embedded in the planar manifold 212, 312 by use of etched channels as will be described below. Thus, and in accordance with another feature of the present invention, the planar manifold assembly 210, 310 may be configured to perform many of the fluid-handling functions necessary for accurate operation of the pneumatic detector 224.

A few principles of operation of the electronic pressure control system operative in the Figures may be understood as follows. The valve 222 is preferably provided as a proportional control valve that is open or closed incrementally to maintain a desired pressure, with the change in open area approximately proportional to the change in controlling voltage supplied to the valve. In a forward regulated system, the pressure sensor 226 is located downstream from the valve 222. If the downstream pressure rises slightly, the pressure sensor voltage will rise. This voltage is transmitted to the electronic pressure controller 220. In response, a new control voltage is fed back to the valve 222. The open area in the control valve will be reduced slightly, resulting is a slightly smaller flow through the valve and a slightly lower pressure at the pressure sensor. This feedback process occurs at relatively high frequency, resulting in very accurate and repeatable pressure control. The following description of the invention also contemplates use of electronic mass flow control, which is very similar in principle to electronic pressure control and can be based on either a proportional control valve or a modulating (on/off) control valve.

A preferred version of closed-loop electronic pneumatic control of pressure and volumetric flow rate may be provided in a preferred embodiment electronic pressure controller that is commercially available in a Hewlett-Packard 6890 Series GC system. The electronic pressure controller 220 also allows control of a plurality of system functions, e.g., configuring either forward or back pressure regulation.

Certain pressure/flow calculations that are largely determined and implemented by the electronic pressure controller 220 in carrying out the teachings of the present invention will now be described. Although pressure is the variable that is controlled and directly measured in the electronic pressure controller, the variables of flow and linear velocity are useable as well because of certain well-understood relationships between pressure and flow in capillary GC. Measurements of both flow and linear velocity can be related to the values calculated and used by the electronic pressure controller. In particular, the Poiseuille equation for flow through a capillary column may be used to calculate the flow of fluids through a tube of circular cross section, where the diameter of the tube is large compared to the mean free path in the fluid. The Poiseuille equation describes the volumetric rate of flow measured at the tube outlet, and can be used to calculate the carrier gas flow rate through a separation column provided in the form of an open tubular column. Because volumetric flow and gas volume depends on pressure and temperature, it is important feature of the contemplated electronic pneumatic controller to calculate and accurately control the measurement conditions. For a given set of operating conditions such as column length and id, carrier gas type, temperature, inlet and outlet pressure, certain such equations are used to calculate volumetric flow rate for a known inlet pressure, or the pressure setting needed to give a desired volumetric flow rate.

The contemplated electronic pneumatic controller can, for example, control volumetric flow rate through a modulating control valve or a proportional control valve. For either type of valve, system feedback control is provided by an electronic pressure sensor incorporating electronic signal processing electronics. A desired pressure may be set; pressure setpoints may be converted to the flow and average linear velocity values necessary, according to calculations performed by the electronic pressure control. Furthermore, the pressure sensors and flow rate sensors described herein will afford a degree of precision in controlling the volumetric flow rate that is significantly improved over the flow control used in prior art pneumatic detectors. For example, the solid-state pressure sensors contemplated for use in the present invention combine temperature compensating circuitry with digital control for extremely accurate pressure control.

Hence, in a departure from the prior art, and because of these above-described relationships, the contemplated electronic pressure control can make use of advanced pressure control technology to control the flow of the fluid stream subject to detection by the pneumatic detector described herein, such that the pneumatic detector will exhibit an improved detector response in comparison to pneumatic detection methods and apparatus in the prior art.

Figure 4:
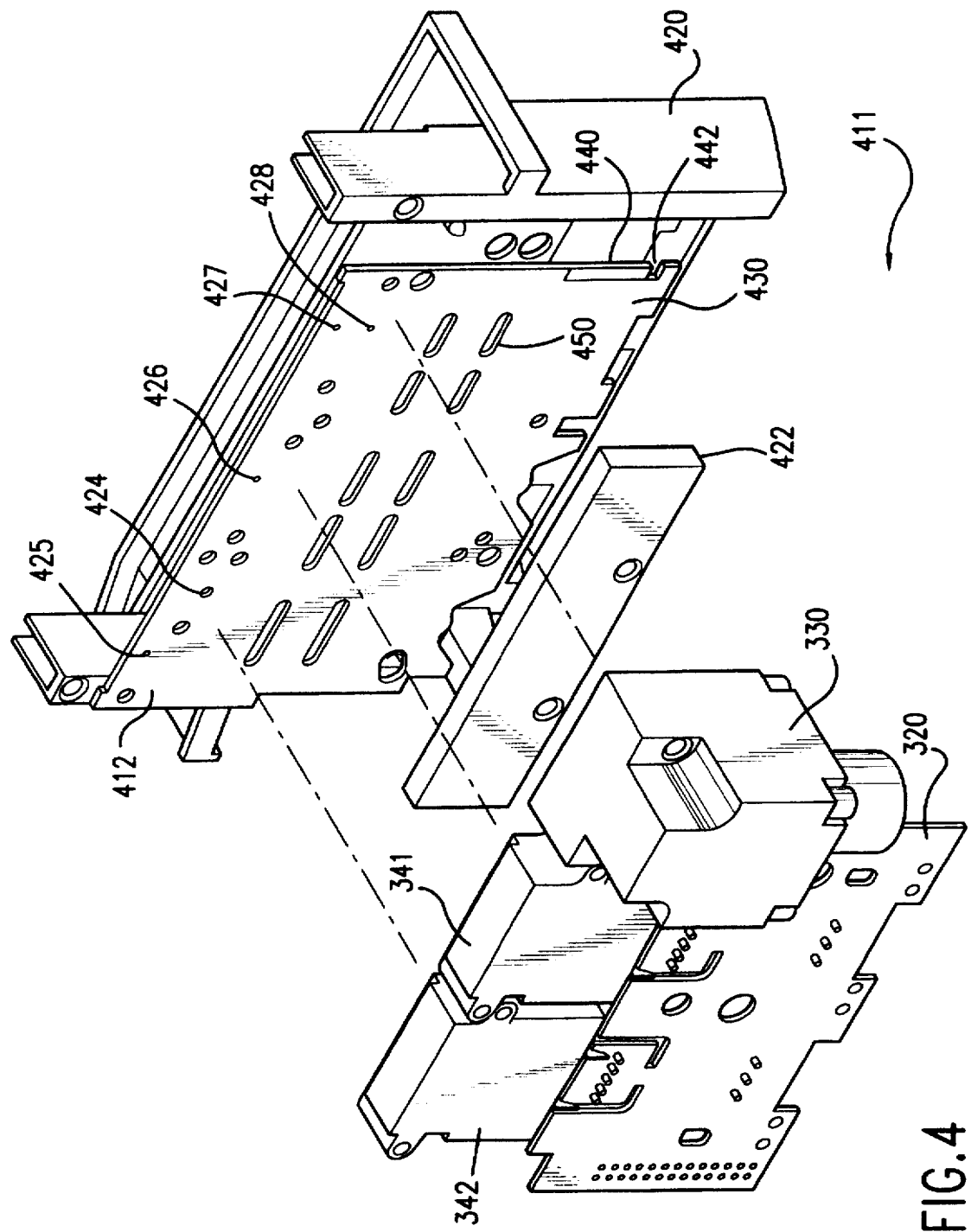
FIG. 4 is a side perspective view of a preferred embodiment of a planar manifold assembly operable in the chromatograph of FIG. 2.

FIG. 4 illustrates in greater detail a portion 411 of the planar manifold assembly 210 of FIG. 2. With reference again to FIG. 3, however, it should be understood that the description and teachings to follow may be applied as well to the construction of the planar manifold assembly 312 for use with a similar array of fluid-handling functions associated with the operation of respective surface-mounted fluid-handling functional devices.

The planar manifold assembly portion 411 includes planar manifold 412, a manifold chassis 420, a backing plate 422, a data and control signal interface board 320, and a variety of fluid handling functional devices, such as a flow controller 330, a first sensor 341, and a second sensor 342. In the preferred embodiment, the flow controller 330 is constructed as a volumetric fluid flow rate controller; the first sensor 341 is constructed as a pressure sensor and the second sensor 342 is constructed as a flow sensor. Further, the planar manifold 412 is constructed to receive carrier gas from a supply fitting and supply line (not shown). The supply fitting attaches to a port surface in the fitting block so as to transfer a flow of carrier gas from the fitting block into the planar manifold 412. The supply fitting also includes an internal frit (not shown). That is, the fitting block and the fluid-handling functional devices are constructed to include internal, fluid-bearing passageways that are accessible at respective ports on their surfaces; each port is recessed to allow use of O-rings for face-sealing the fitting block or fluid-handling functional device to the planar manifold 412. Each port receives a respective O-ring when mated to respective ports 414 on the planar manifold 410.

The fluid-handling functional devices are clamped to the planar manifold 412 with the aid of suitable means known in the art, such as fasteners (not shown), that pass through appropriate through-holes in the planar manifold 412, so as to be secured by suitable means.

Further details on the planar manifold assembly 411 contemplated by the present invention will be found with reference to a similar planar manifold assembly disclosed in commonly-assigned U.S. Pat. No. 5,567,868, entitled "Planar Manifold Assembly" and issued to Craig et al.

In the preferred embodiment of the planar manifold 412, a front plate 430 and a rear plate 440 may be sized and constructed to be superimposed and bonded together during the manufacturing process to form the planar manifold 212. Preferably, the front plate 430 and rear plate 440 are each machined from stainless steel and one or both of the plates are etched to provide an arrangement of channels, each capable of bearing a fluid stream, before the plates are bonded together. The preferred method of bonding is diffusion bonding, which generally is known in the art and is described in, for example, U.S. Pat. No. 3,530,568, the disclosure of which is included herein by reference. However, in other embodiments, other materials and bonding methods may be employed, and a number of intermediary plates (such as one, two, or more, not shown) are also contemplated being provided intermediate the front plate 430 and rear plate 440 to form a multi-layer configuration. The channels are arranged to be in fluid communication with respective ports located at one of the major surfaces of at least one of the front and rear plates 430, 440, such that the ports may be accessed at the exterior of the planar manifold 412 when assembled.

For example, the front plate 430 include features so as to receive certain fluid-handling functional devices already described. In particular, to accommodate attachment of the flow sensor 342, there is provided a pneumatic input port 425 and pneumatic output port 424; to accommodate the pressure sensor 341, there is provided a pneumatic output port 426; to accommodate attachment of the flow controller 330, there are provided a pneumatic input port 427 and pneumatic output port 428; each of the aforementioned ports communicate with respective pneumatic channels (not shown) in the planar manifold 412.

A notch 442 in the rear plate 440 is included at manufacture to correspond with one of several indicia inscribed on the front plate 430 so as to define a particular pneumatic configuration that is served by the planar manifold 412. In the illustrated embodiment, the notch indicates by its location that the planar manifold 412 is intended for use in a pneumatic detector configuration. It is another feature of the present invention that the construction of the front plate 430 is common to all of the configurations, and that the rear plate 440 will vary in its construction according to the type of configuration that is to be served. This feature thus makes the front plate 430 a more versatile piece part, thus lowering the parts count and reducing manufacturing costs. In addition, the location of the notch can be sensed during assembly of the planar manifold assembly 411 to ensure that the planar manifold 412 has been properly configured for the pneumatic detector configuration.

Each of the front plate 430 and the rear plate 440 include a certain other physical features for accommodating respective mechanical or pneumatic functions. Oblong openings 450 are distributed longitudinally to effect a thermal break between the plate upper portions and the plate lower portions.

FIGS. 5A–6C illustrate exemplary embodiments of orifice structures for use in a pneumatic detector constructed according to the present invention. In these embodiments, the orifice is located in such a fashion as to be closely adjacent (or integrated within) a pressure sensor so as reduce the effects of fluid viscosity on the pressure sensed at the orifice, while enhancing the response of the pressure sensor to the fluid density of the fluid stream passing through the pressure sensor. The depth and width of the orifice is made to be sufficiently small such that the orifice is operable in a mode described in fluidic theory as being characteristic of a "sharp-edged" or "knife-edged" orifice. These embodiments are thus contemplated as realizing the theoretical advantages of a sharp-edged orifice in a pneumatic detector in a fashion superior to those in the prior art. These embodiments are also contemplated as offering more accurate reading of the pressure at the orifice than may be found in the art. As a result, the pneumatic detector constructed according to the present invention is believed to offer improved sensitivity to the molecular weight of the fluid stream passing through the orifice. Accordingly, the molecular weight of the sample/fluid mixture may be determined by the chromatograph such that the composition of the sample/fluid mixture is detected.

In the embodiments to follow, the desired sharp-edge orifice is contemplated as being provided in a transducer diaphragm composed of piezoresistive material such as doped silicon, silicon carbide, or similar material. However, the invention contemplates the use of other transducer methodologies, including transducers responsive to an applied pressure that generate a representative output signal according to capacitance and optical effects.

Figure 5A:
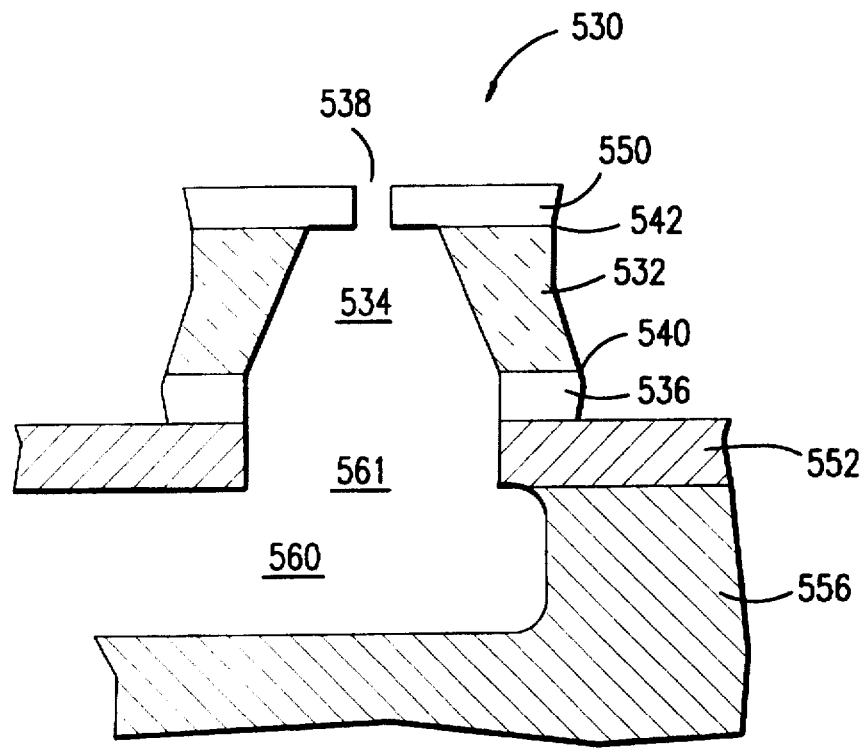
FIG. 5A is a side section view of a central portion of an exemplary micromachined orifice chip contemplated for use in a fluid-handling functional device on the planar manifold assembly of FIGS. 2-4, with certain portions of the orifice chip being omitted for clarity.

FIG. 5A illustrates a preferred embodiment of a micromachined orifice chip is formed from a doped silicon die is micromachined to provide an orifice 538. The microminiature orifice chip 530 is mounted on the planar manifold 562 wherein the front plate 552 includes a sufficient opening 561 to communicate with an etched channel 560. The orifice chip 530 is located over the opening 561 and is anodic bonded to the outer surface of the front plate 552. The orifice chip 530 includes a support substrate 532 which is fabricated in silicon on a base layer 516 of silicon nitride. A central flow via 534 is formed through the support substrate 512, a silicon nitride or silicon dioxide upper layer 550, and silicon nitride or silicon dioxide base layer 536. The support substrate 512 is preferably a silicon chip which has been fabricated from a wafer using batch processing steps, and includes an orifice 538 etched in the layer 550. The microminiature orifice chip 530 is approximately 7 mm by 7 mm, but this is not critical. The support substrate 532 is approximately 400 microns thick. In a preferred embodiment, the orifice 538 is square and has each side provided in the range of 20 to 200 microns, and preferably is provided in the range of 20 to 50 microns on each side.

Figure 5B:
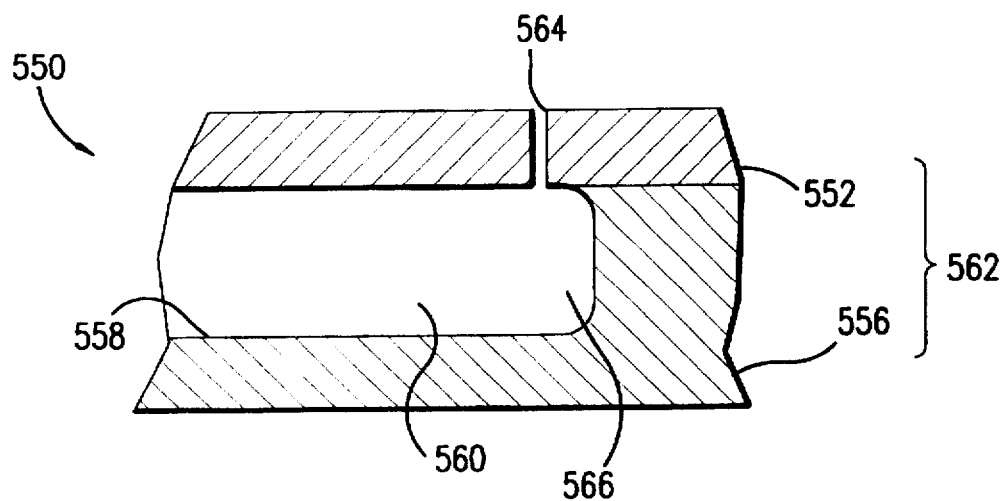
FIG. 5B is a side sectional view of a terminal portion of a combination etched channel and orifice contemplated for use in a planar manifold in the planar manifold assembly of FIGS. 2-4.

FIG. 5B illustrates an embodiment of an orifice structure constructed within a planar manifold, such as the planar manifold 412 of FIG. 4. The front and rear plates 552, 554 include respective through-hole 564 and etched section 558. The front and rear plates 552, 554 combine to form a pneumatic channel 560 when the front and rear plates are aligned, superimposed, and bonded together to form a planar manifold 562. Through-hole 564 is drilled or etched by suitable means to provide fluid communication between the terminal section 566 of the channel 560 and the exterior of the front plate 552. In a preferred embodiment, the through-hole 564 is provided in the range of 20 to 200 microns diameter, and preferably is provided in the range of 20 to 50 microns diameter. In some applications, the channel 560 may be integral with the embedded separation column 350 as shown in FIG. 3.

Figure 6A:
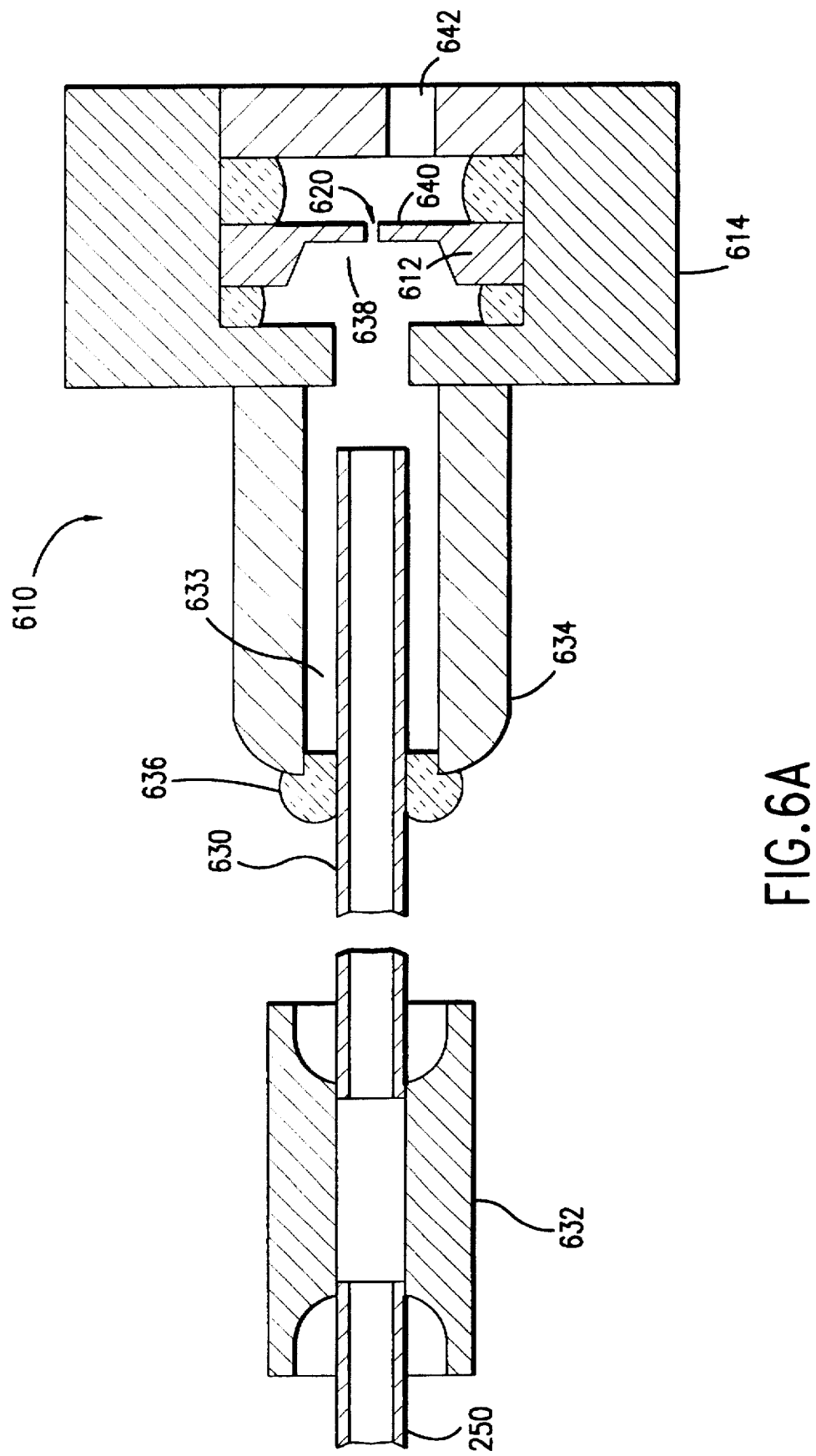
FIG. 6A is a side sectional view of a fluid-handling functional device connectable to the separation column for providing in one device both means for pressure sensing and the provision of an orifice, wherein a diaphragm member responsive to pressure includes an orifice in a central portion of the diaphragm member.
Figure 6B:
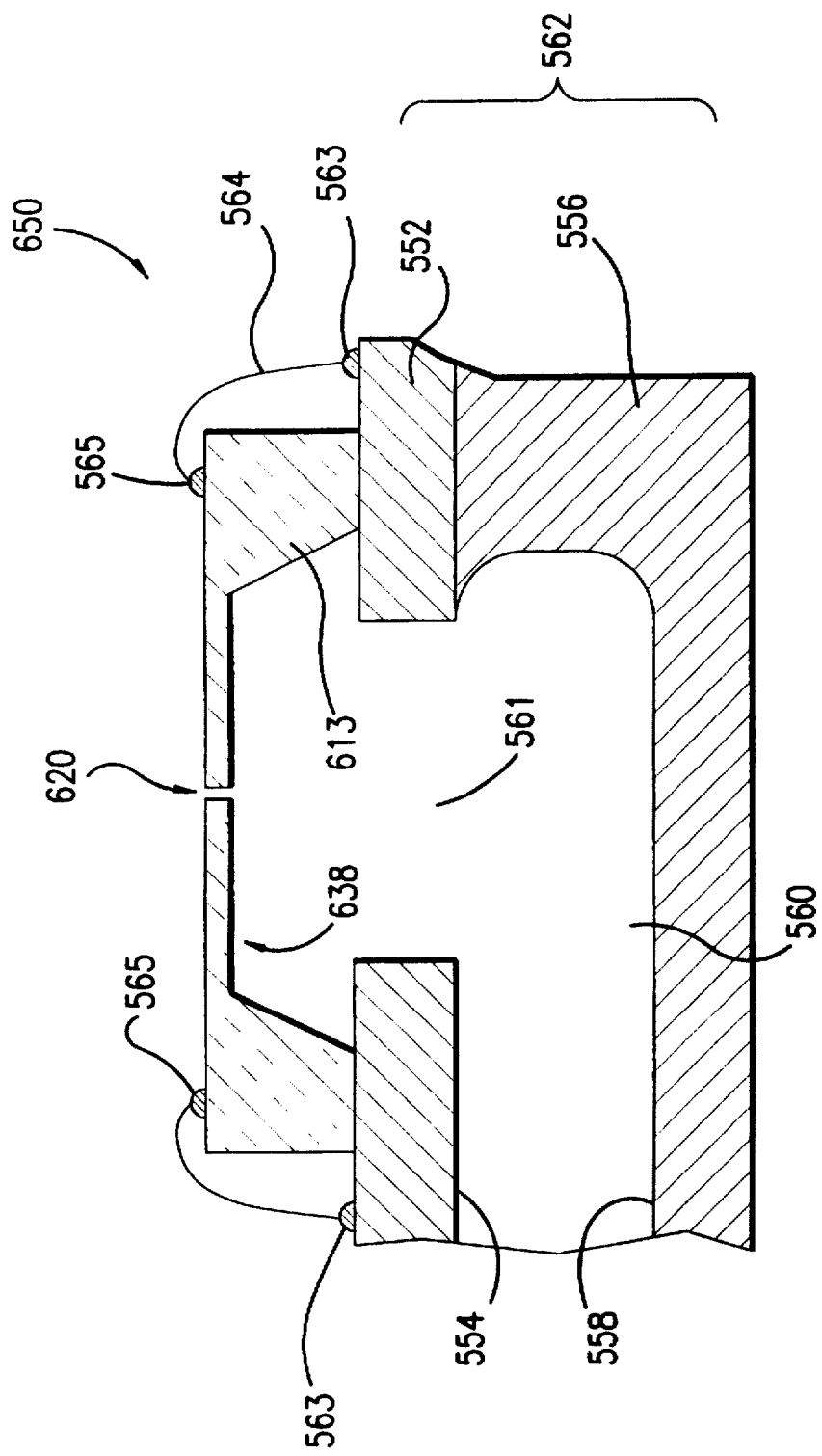
FIG. 6B is a side sectional view of a terminal portion of a combination etched channel and a micromachined orifice chip contemplated for use on a planar manifold in the planar manifold assembly of FIGS. 2-4.
Figure 7:
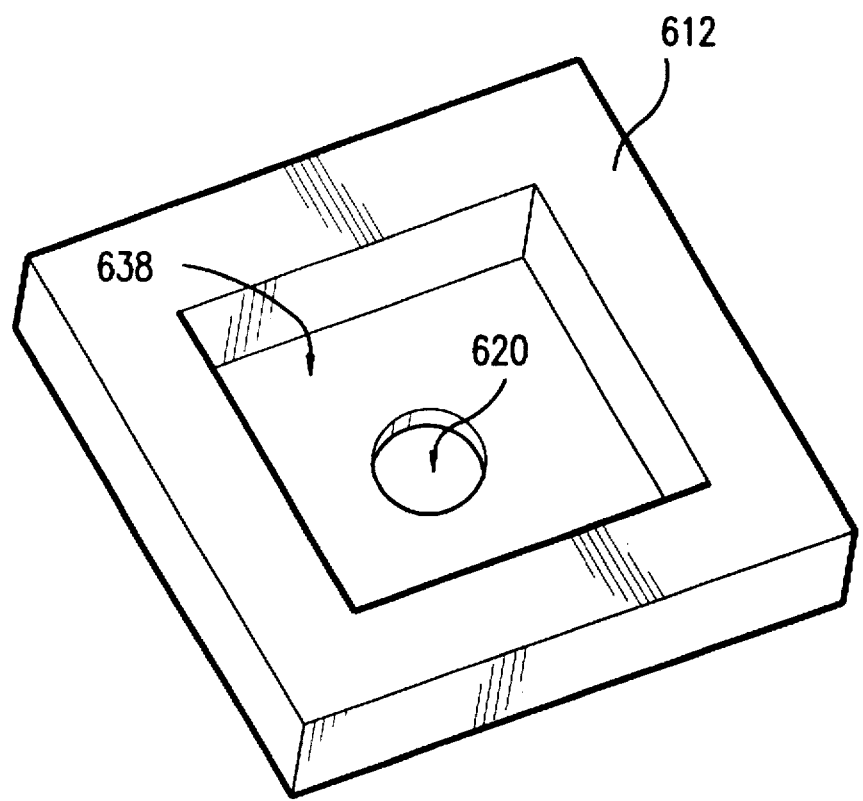
FIG. 7 is a side perspective view of the diaphragm member operable in the fluid-handling functional devices of FIG. 6A-6C.

FIGS. 6A–6C are a side sectional views of preferred embodiments of a preferred fluid-handling functional device that is contemplated for use with the arrangement illustrated in FIG. 2 for providing, in a single device, both a sharp-edged orifice and means for sensing the pressure developed at the orifice. In FIG. 6A, the fluid-handling functional device is constructed as a modified pressure sensor 610, wherein a diaphragm member 612 is mounted in suitable base structure 614 and is responsive to pressure such that an output signal representative of pressure on the diaphragm member may be output from suitable means such as a piezoelectric component (not shown), in the pressure sensor 610. In accordance with a particular feature of the present invention, the diaphragm member 612 includes an through-hole 620 in a central portion of the diaphragm member 612. The column effluent is directed through the column 250 and into a disposable section of guard column by use of a union 632. The guard column 630 is inserted into the hollow bore 633 of a sensor inlet 634 and is sealed with a sealant 636 such that the column 250 is placed in fluid communication with the inlet side 638 of the diaphragm member 612. The effluent fluid stream that flows from the column 250 is thereby directed to the inlet side 638, passes through the through-hole 620, and is discharged to ambient atmosphere by way of an outlet vent 642. As further understood with reference to FIG. 7, an experimental prototype of the illustrated pressure sensor 610 was constructed by modification of a Model 24PCA solid-state gage pressure sensor manufactured by the Micro Switch Division of Honeywell Inc., Freeport, Ill. The diaphragm member 612 was removed from the pressure sensor and the through-hole 620 was created by use of an extremely narrow beam from an excimer laser. The resulting through-hole 620 has an approximate average diameter of 50 micrometers and exhibits the desired properties of a sharp-edged orifice.

FIG. 6B includes another preferred embodiment wherein a doped silicon die 638 that is micromachined to provide a diaphragm member 613 is mounted on the planar manifold 562 wherein the front plate 552A includes a sufficient opening 561 to communicate with the channel 560. The diaphragm member 613 is located over the opening 561 and is anodic bonded to the outer surface of the front plate 552A such that the diaphragm member 613 is responsive to pressure in the channel 560; an output signal representative of pressure on the diaphragm member may be output from wires 564 bonded between conductive pads 563, 565. In accordance with a particular feature of the present invention, the diaphragm member 613 includes an through-hole 620 in a central portion of the diaphragm member 613. The column effluent is directed through the channel 560 and is discharged to ambient atmosphere by way of the through-hole 620 which thus acts as a sharp-edged orifice. In some applications, the channel 560 may be integral with the embedded separation column 350 as shown in FIG. 3.

FIG. 6C includes another preferred embodiment 660 attachable directly to the effluent stream of interest, wherein the doped silicon die 638 (having a diaphragm member 613) is flipped and is mounted using conductive elastomeric pads 695 to a support 690 having a vent 680 to communicate the effluent to ambient atmosphere. The diaphragm member 613 is located over the vent 620 and is hermetically bonded by, e.g., metal diffusion techniques, to a short section of borosilicate glass capillary tubing 670 such that the diaphragm member 613 is responsive to pressure of a fluid stream present in a bore 672 of the borosilicate glass capillary tubing 670. The outlet end of the separation column 250 may be connected to a distal end (not shown) of tubing 670 by means such as the union 632 (FIG. 6A). The output signal representative of pressure on the diaphragm member may be output from pads 695 directly to signal interface electronics on an ancilliary electronic circuit board. The column effluent is directed through the bore 672 and is discharged to the vent 680 by way of the through-hole 620 which thus acts as a sharp-edged orifice.

The advantages of the planar manifold assembly of the present invention include the reduction of external connections between fluid-handling functional devices (such as fittings, valves, sensors, and the like) by use of a single planar manifold for the provision of a plurality of flow paths. The fluid-handling functional devices that connect to the planar manifold are preferably constructed to be surface-mounted, which has been found to offer reliable, fluid-tight connection without dead volume of conventional pneumatic connections. The number and complexity of external connections, which would otherwise undesirably increase the volume of the flow system, are also decreased.

A further advantage of the present invention is that multiple fluid-handling functional devices may be coordinated and assembled in a smaller volume than is possible in prior art systems. This results from the pneumatic channels that are integrated in the planar manifold, and thus many of the fluid flow paths are integral to the planar manifold. A large number of fluid-handling functional paths may be integrated into the planar manifold that heretofore would be difficult if not impossible to assemble using conventional techniques.

EXPERIMENTAL DATA

Figure 8:
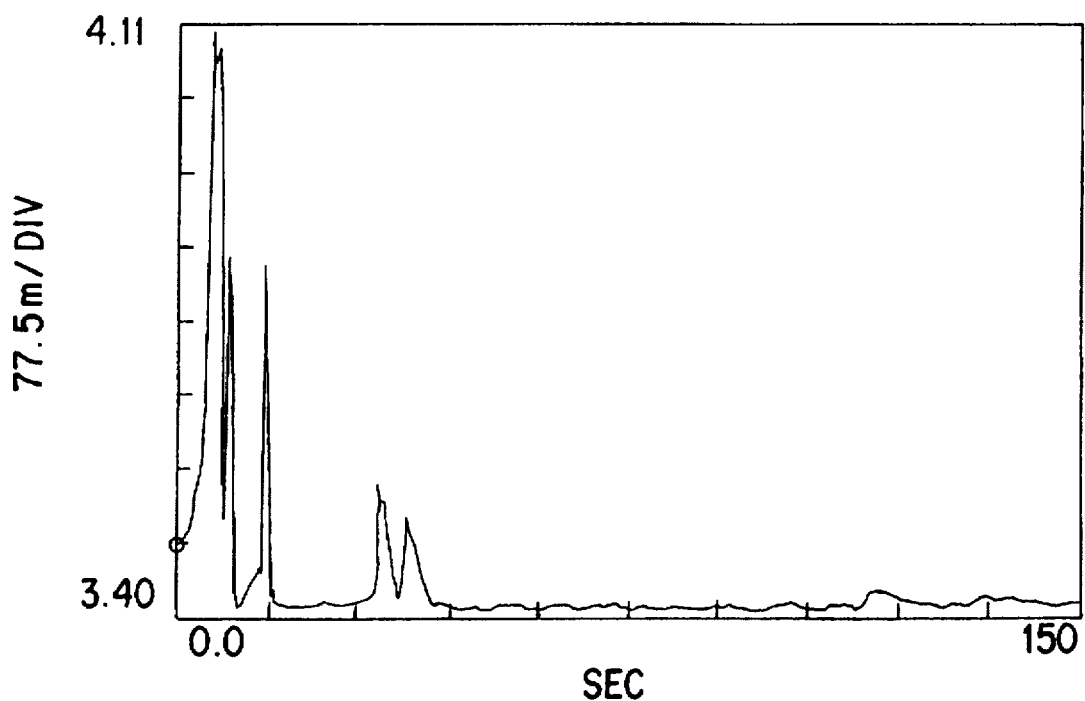
FIGS. 8 and 9 are exemplary representations of the detector response to a known sample that was obtained from a pneumatic detector in an experimental version of a chromatograph constructed according to the present invention.
Figure 9:
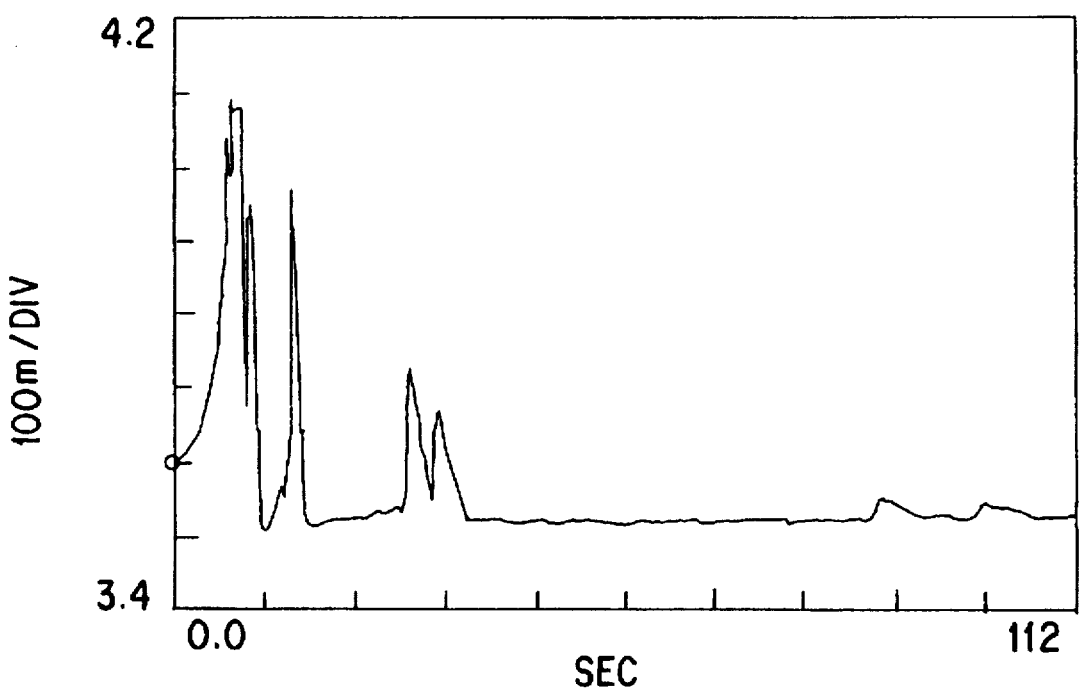

An experimental version of the chromatograph 100 shown in FIG. 1 was constructed using a Hewlett-Packard 6890 Gas Chromatograph and equipped with microminiature orifice chip similar to the pressure sensor 610 illustrated in FIG. 6A. The orifice provided in the orifice chip was a square opening having a width of 75 micrometers. The chromatograph was operated to perform an analysis of injected samples of natural gas. Each sample quantity was 250 microlitres (uL) of a Qualitative Test Sample, Natural Gas, part no. 5080-8756, supplied by Hewlett-Packard Company, Wilmington, Del. This sample has an approximate composition as follows: 69% Methane, 9% Ethane, 6% Nitrogen, 6% Propane, 3% is-Butane, 3% n-Butane, 1% Carbon Dioxide, 1% is-Pentane, 1% n-Pentane, 0.5% Hexane, 0.5% Oxygen. The separation column 114 was a HP Alumina Plot Column (part no. 19095P-S25) having a length of 50 meters and an internal bore diameter of 530 micrometers, operated at a carrier flow rate of 60 mL/min. In a first analytical run, the results of which are shown in FIG. 8, the oven temperature was set at 90 degrees centigrade; in a second analytical run, the results of which are shown in FIG. 9, the temperature was set at 100 degrees centigrade. Although the injection volume and carrier flow rate were higher than would be considered as optimal, the resulting detector output signal accurately represented the separation and detection sample components $C_1$ through $C_6$ that were present in the injected sample. A high flow rate was found to be required for adequate sensitivity.

Linearity, detection limit and dynamic range are important parameters to determine if the contemplated detection method is of practical use. All three are strongly dependent on the operating condition of the chromatography system. To study linearity and detection limit, the system shown in FIG. 2 was used. The pressure sensor range was further reduced to 1 PSI full scale. Since the sensitivity of this detector increases with carrier flow rate, a nominal 50 mL/min. was picked. Oven temperature was set at 50 degrees C. since no separation was required for air injection.

Linearity data was obtained by successively injected different volumes of analyte and measuring the area of the detection. Table 1 shows the area count vs. injection volumes for successive injections of air into the carrier fluid at injection sample volumes of 1 uL to 100 uL. As may be seen, the detector response is very linear.

TABLE 1

| Peak Area vs. Injection Volume. | | | | | | |
|---|---|---|---|---|---|---|
| Injection Volume (uL) | 1 | 2 | 5 | 10 | 50 | 100 |
| Peak Area (mV sec) | 17.06 | 35.85 | 82.83 | 177.43 | 1095.52 | 1761 |

The detection limit of the pneumatic detector at a given condition with known injection volume can be derived using a detector response peak having a shape that approximates a Gaussian. The peak concentration is represented by the relationship:

$$(Vinj)/[(Flow\ rate)(sigma)(square\ root\ of\ Pi)]$$

where (sigma) is the standard deviation of the Gaussian peak shape. For a 1 uL injection volume of air, the detector responded with a peak signal of 17.5 mV having a peak width of about 6.82 seconds. The detection limit peak concentration was then calculated to be:

$$1\ uL\ /[(50\ mL/min)(sqrt(Pi))(6.82\ sec/6)] = 596\ ppm$$

The dynamic range of contemplated pneumatic detector is believed to depend strongly on the constancy of the carrier flow rate and the particular molecular weight of the analyte that is subject to detection. A higher molecular weight analyte is expected to cause a larger detector output signal. Greater detector sensitivity has been achieved by increasing the column flow rate. A decrease in the carrier flow rate can also increase the dynamic range but at the expense of detector sensitivity.

Higher molecular weight compounds tend to elute slowly, as they are subject to greater diffusion and elute at a lower concentration. Detection of high molecular weight compounds may require an increase in detector sensitivity and signal-to-noise ratio to compensate for their lower concentration.

It is postulated that the required flow rate for a given minimum detection level is inversely proportional to the area of the orifice. Thus, decreasing the linear dimension of the orifice by half could allow a reduction in the flow rate by a factor of four, yet maintain a minimum detection level. It is contemplated that use of sharp-edged orifice structures, especially those illustrated in FIGS. 5A–6C, offer a smaller diameter orifice and allow operation of the detector at a lower carrier flow rate. It is further postulated that a smaller injection volume can be advantageously used with a lower carrier flow rate and a smaller orifice.

The chromatographs illustrated in FIGS. 8 and 9 were obtained using an isothermal oven condition. Further experimental runs were obtained while sensing of the oven cavity temperature; minute temperature variations were observed to cause a corresponding variation in the detector output signal. These results indicate that improved control of the constancy of the oven temperature will yield less noise in the detector output signal, and accordingly greater signal-to noise ratio. Further, it is contemplated that temperature programming can be implemented during a run if the column fluid stream is subject to flow rate control rather than pressure controlled.

A false peak is detected at the detector during injection. This peak can be minimized by programming the electronic pressure control for pressure control of the column fluid stream during injection followed by flow control of the column fluid stream during the remainder of the analytical run. Alternatively, the false peak can be used to synchronize the beginning of an analysis.

While the invention has been described and illustrated with reference to specific embodiments, those skilled in the art will recognize that modification and variations may be made without departing from the principles of the invention as described herein above and set forth in the following claims.

What is claimed is:

1. A chromatograph, comprising:

an injector for receiving a sample and a pressurized carrier fluid flow and in response providing a sample/ fluid mixture;

a separation column connected to the injector and located in a temperature-controlled zone for receiving the sample/fluid mixture and for providing a column effluent stream;

a pneumatic detector having an orifice, means for receiving the effluent stream and for directing the effluent stream through the orifice and a pressure sensor having a diaphragm for sensing a change in the pressure of the effluent stream at the orifice in response to a change in the density of the effluent stream passing through the orifice and for generating a representative output pressure signal, whereby one or more characteristics of the effluent stream that are related to the density of the effluent stream are represented by the output pressure signal, and wherein the orifice is integrated in the diaphragm such that the output pressure signal is responsive to the pressure of the effluent stream at the orifice; and an electronic pneumatic controller including means for controlling the volumetric flow rate of the carrier fluid.

2. The chromatograph of claim 1, further comprising means for controlling the temperature of the temperature-controlled zone whereby unwanted flow rate variation in the fluid stream is reduced.

3. The chromatograph of claim 1, wherein the electronic pneumatic controller further comprises means for sensing an input pressure of the separation column and for generating a respective input pressure signal and wherein the electronic pneumatic controller includes means for controlling carrier fluid flow rate that is responsive at least one of the input and output pressures whereby unwanted flow rate variation in the fluid stream is reduced.

4. The chromatograph of claim 1, further comprising a planar manifold assembly having a planar manifold operably connected to a selected one of said injector, separation column, and pneumatic detector, and wherein said selected one of said injector, separation column, and pneumatic detector is mounted on the planar manifold assembly and pneumatically connected to one or more fluid streams carried in a channel embedded in the planar manifold.

5. The chromatograph of claim 4, wherein the pneumatic detector is connected to the channel at a surface port and the orifice is integrated into a component portion of a fluid-handling functional device selected from the group consisting of: the pneumatic detector and the surface port.

6. The chromatograph of claim 4, wherein said selected one of said injector, separation column, and pneumatic detector is adapted for surface mounting to the planar manifold.

7. The chromatograph of claim 1, wherein the pneumatic detector includes an orifice provided in the form of a sharp-edge orifice.

8. The chromatograph of claim 1 wherein the pneumatic detector is integrated in a surface port on the planar manifold.

9. The chromatograph of claim 8 wherein the surface port is in fluid communication with a serpentine channel adapted for operation as the separation column.

10. The chromatograph of claim 4, wherein the diaphram is integrated in a component portion of a fluid-handling functional device mounted on the planar manifold, whereby the component portion is in fluid communication with the column effluent fluid stream via said channel in the planar manifold, such that the orifice is integral with the fluid-handling functional device.

11. The chromatograph of claim 1, wherein the orifice is provided in a component portion of a micromachined orifice chip.

12. The chromatograph of claim 1, further comprising a planar manifold assembly having a planar manifold operably connected to a selected one of said injector, separation column, and pneumatic detector, and wherein the planar manifold is adapted for carrying a fluid stream in a channel embedded in the planar manifold, and wherein the pneumatic detector is in fluid communication with the channel in the planar manifold.

* * * * *